US006849439B2

(12) United States Patent
Henson et al.

(10) Patent No.: US 6,849,439 B2
(45) Date of Patent: Feb. 1, 2005

(54) MODIFIED BARLEY $\alpha$-GLUCOSIDASE

(75) Inventors: Cynthia A. Henson, DeForest, WI (US); Elizabeth H. Muslin, Madison, WI (US); Suzanne E. Clark, Madison, WI (US)

(73) Assignees: Wisconsin Alumni Research Foundation, Madison, WI (US); The United States of America as represented by the Secretary of Agriculture, Washington, DC (US)

( * ) Notice: Subject to any disclaimer, the term of this patent is extended or adjusted under 35 U.S.C. 154(b) by 46 days.

(21) Appl. No.: 10/043,418

(22) Filed: Jan. 10, 2002

(65) Prior Publication Data

US 2002/0184662 A1 Dec. 5, 2002

Related U.S. Application Data

(60) Provisional application No. 60/260,787, filed on Jan. 10, 2001.

(51) Int. Cl.[7] .......................... C12N 9/00; C12N 9/24; C07K 1/00; C07H 21/04

(52) U.S. Cl. .............................. 435/200; 435/4; 435/6; 435/69.1; 435/183; 435/200; 435/210; 435/440; 435/455; 435/468; 536/23.2

(58) Field of Search .............................. 435/4, 6, 69.1, 435/183, 200 T–210, 440, 455, 468, 252.3, 320.1; 536/23.2 T

(56) References Cited

U.S. PATENT DOCUMENTS 5,763,252 A 6/1998 Skadsen et al.

OTHER PUBLICATIONS

Frandsen et al. (Plant Physiol., 2000, vol. 123:275–282).*
Nakao et al. (Eur. J. Biochem., 1994, vol. 220(2):293–300).*
Scandurra et al. (Biochimie, 1998, vol. 80(11) :933–941).*
Li et al. (Protein Engg., 1997, vol. 10(10) :1199–1204).*
Igarashi et al. (Biosci. Biotechnol. Biochem., 1999, vol. 63(9): 1535–1540).*

* cited by examiner

*Primary Examiner*—Manjunath N. Rao
(74) *Attorney, Agent, or Firm*—Quarles & Brady LLP

(57) ABSTRACT

Barley $\alpha$-glucosidase is an important enzyme in the conversion of barley starch to fermentable sugars during the industrial production of ethanol, as in brewing and fuel ethanol production. The enzyme is, however, relatively thermolabile, a disadvantage for an enzyme useful in industrial processes which are preferably conducted at elevated temperatures. Site directed mutagenesis has been conducted to make mutant forms of barley $\alpha$-glucosidase which have improved thermostability. The sites for this site-directed mutagenesis were selected by sequence comparisons with the sequences of other $\alpha$-glucosidase proteins which are more thermostable. The recombinant mutant enzymes thus produced have been demonstrated to improve the thermostability of the enzyme.

2 Claims, 6 Drawing Sheets

```
BARLEY   MA------T/CV---------LLLCLCLCLFAFRLCSSKEECFLAAR---  (32)
S.BEET   Me-----rskipryicptlavvLptvLCmvvegatrSKndrqgeAigyg  (46)
SPINACH  Mkkk:psla1Gi---------LLvfLlqyLvAgiztSendpegvigy---  (38)
ARABID.  Me------slhwfpnif----lvvvffeLrssqvvleeEEstvvgy---  (37)

BARLEY   -----TVLAVAVTMEG-----ALRAEAATGGRSSTG------DVQRLAVY  (66)
S.BEET   yqvknakvdnstgks------tallqlirnspvygp------Dihf:sft  (35)
SPINACH  -----gykvksVkvds-----gtRrs:talpqlvknssvygpDiQlteit  (78)
ARABID.  -----gyvvreVgvdsnrqvltakldlikpasvygp------DiksLnlh  (76)

BARLEY   ASLETDSRLRVRIITDADHPRWEVPQDIIPRPAPGD------VLHDAPPA  (109)
S.BEET   ASfEeDdtLRiRfTDAnnrRWEiPnevlPRPpPppspppplaslqRlpkPi  (133)
SPINACH  ASLEendRLRVRITDAKHrRWEiPdnIlhRhqPpp-------ppphelss  (121)
ARABID.  vSLETssRLRiRITDssqqRWEiPetvIPRagnhs-------prrfstee  (119)

BARLEY   S--------S--APLQCRVLSPAGSDLVLTV-H-ASPFRFTVSRRSTGDT  (147)
S.BEET   p--------q--nqptttVLShphSDLafTlfH-ttPFgFTiyRkSThDv  (172)
SPINACH  lyrtllsspt--tnrrkilLShpnSDLtfel-inttPFgFTiSRkSThDv  (168)
ARABID.  d--------ggnsPennflsdPssdlvftlh-n-ttFFgPsVSRRSsGDi  (159)

BARLEY   LFDTAPG-------L-------VFRDKYLEVTSALPAGRASLYGLGEHTK  (183)
S.BEET   LFDatPipsnpttfL-------iykDqYLqlsSsLPAqrAbLYGLGEHTK  (215)
SPINACH  LFDatPdptnpntfL-------iFiDqYLhlTSsLFgtRAhiYGLGEHsK  (211)
ARABID.  LFDTsPd-------ssdsntyfiFkDqfLqlsSALPenRsnLYGiGEHTK  (202)

BARLEY   SSFRLRHNDSFTLWNADIGASYVDVNLYGSHPFYMDVRAP------GTAH  (227)
S.BEET   ptFqLaHNqilTLWNADIasfnrDlNLYGSHPFYMDVRsspm----GstH  (262)
SPINACH  ptFqLaHNqtlTmraADIpsSnpDVNLYGSHPFYMDVRsspva---GstH  (258)
ARABID.  rSFRLipgetmTLWNADtGsenpDVNLYGSHPFYMDVRgskgneeaGTtH  (252)

BARLEY   GVLLLSSNGMDVLYGGSYVTYKVIGGVLDFYFFAGPNPLAVVDQYTQLIA  (277)
S.BEET   GVfLLnSNGMDVeYtGcriTYKVIGGiiDlYiFAGrtPemViDQYIkLIg  (312)
SPINACH  GVLLLnSNGMDVeYtGrriTYKVIGGiiDlYFFAGPsPgqVVeQfTrvIg  (308)
ARABID.  GVLLLnSNGMDVkYeGhriTYnVIGGViDlYvFAGPsPemVmnQYTeLIg  (302)

BARLEY   RPAPMPYWSFGFHQCRYGYLNVSDLERVVARYAKARIPLEVMWIDIDYMD  (327)
S.BEET   RPAPMPYWaFGFHQCRwGYrdVreiEtVVdkYAeARIPLEVMWTDIDYMD  (362)
SPINACH  RPAPMPYWaFGFqQCRYGYhdVyeLqsVVAgYAKAkIPLEVMWIDIDYMD  (358)
ARABID.  RPAPMPYWSFGFHQCRYGYKNVSDLEyVVdgYAKAgIPLEVMWIDIDYMD  (352)

BARLEY   GFKDFTLDRVNFIAAELRPFVDRLHRNAQKYVLILDPGIRVDPIDATYGT  (377)
S.BEET   aFKDFTLDpVhFpldkmqqFVtkLHRNgQrYVpILDPGI---ntnksYGT  (409)
SPINACH  ayKDFTLDpVNFpldkmkkFVnnLHKNgQKYVvILDPGI---stnkTYeT  (405)
ARABID.  GyKDFTLDpVNFpedkmqeFVDtLHKNgQKYVLIIDPGI---gvDssYGT  (399)

BARLEY   FVRGMQQDIFLKRNGTNFVGNVWPGDVYFPDFMHPAAAEFWAREISLFRR  (427)
S.BEET   FiRGMQsnvFiKRNGnpylGsVWPGpVYyFDFldFAArcFWvdEIkrFRd  (459)
SPINACH  yiRGMkhDvFLKRNGkpylGeVWPGpVYFPDFlkPaAltFWtdEIkrFln  (455)
ARABID.  ynkGMeaDvFiKRNGepylGeVWPGkVYFPDFlnPAAAtFWsnEIkmFqe  (449)

BARLEY   TIFVDGLWIDMNEISNFYN--PEPMN--ALDDPPYRINNDGTGRPINNKT  (473)
S.BEET   ilPiDGiWIDMNEaSNFiceaPtPgs--tLDnPPYkINNsGgrvPINsKT  (507)
SPINACH  llFVDGLWIDMNEISNFis--spPipgstLDnPPYkINNsGvmlPI:NKT  (503)
ARABID.  ilFlDGLWIDMNEISNFit--splssgeeLDDPPYkINNsGdkRPINNKT  (497)

BARLEY   VRFLAVHYGGVTEYEEHNLFGLLEARATGRGVLRDTGRRPFVLSRSTFVG  (523)
S.BEET   ipatAmHYGnVTEYnaHNLyGfLEsqATrealvRpatRgPF:LSRSTFaG  (557)
SPINACH  ipFtAmHYGdipEYnvHNLFGyLEARvTrsalik!TekRPFVLSRSTFsG  (553)
ARABID.  VpatsiHfGnisEYdaHNLyGLLEAkAThqaVvd:TGkRPFiLSRSTFVs  (547)

BARLEY   SGRYTAYWTGDNAATWGDLRYSINTMLSFGLFGMPMIGADICGFNGNTTE  (573)
S.BEET   SGkYTAhWTGDNAArWdDLqYSIpTMLnFGLFGMPMIGADICGFaesTTE  (607)
SPINACH  SGkYTAhWTGDNAATWnDLvYSIpsMLdFGLFGiPMvGADICGFlGNTTE  (603)
ARABID.  SGkYTAhWTGDNAAkWeDLaYSIpgilnFGLFGiPMvGADICGFshdTTE  (597)

BARLEY   ELCGRWIQLGAFYPFSRDHSAIFTVRRELYLWFSVAASGRKALGLRYCLL  (623)
S.BEET   ELCcRWIQLGAFYPFSRDHSArdTthqELYLWeSVAASaRtvLGLRYcLL  (657)
SPINACH  ELCrRWIQLGAFYPFSRDHSslgTtyqELYrWeSVAASaRKvLGLRYcLL  (653)
ARABID.  ELCrRWIQLGAFYPFsRDHSs:gTaRqELYLWdSVAesaRKVLGLRYrLL  (647)
```

FIG 2

```
BARLEY    PYFYTLMYEAHMTGAPIARPLFFSYPHDVATYGVDRQFLLGRGVLVSPVL  (673)
S.BEET    PYYYTLMYdAnlrGsPIARPLeFtfPdDVATYGissQFLiGRGimVSPVL  (707)
SPINACH   PYFYTLMYEAqlnGiPlARFLFFSfPdDikTYGiasQFLLGkGVmVSPVL  (703)
ARABID.   PhlYTLMYEAHvsCnPIARPLFFSfFqDtkTYeiDsCFLiGksimVSPaL  (697)

BARLEY    EPGPTTVDAYFPAGRWYRLYDYSLAVATRTGKHVRLPAPADTVNVHLTGG  (723)
S.BEET    qPGssiVnAYsPrGnWveLenYtesVsvsaGtyVsLsAPpDhiNVHiheG  (757)
SPINACH   kPGvvsVtAYFPrGnWfdLfDYtrsVtasTGryVtLsAPpDhiNVHiqeG  (753)
ARABID.   kqGavaVDAYFPAGnWfdLfnYSfAVggdsGKHVRLdtPADhVNVHvreG  (747)

BARLEY    TILPLQGSALTTSRARRTAFHLLVALAEDGTASGYLFLDDGDSPEYGR-R  (772)
S.BEET    nIvamQgeAmTfqaARsTpFHLLVvmsdhvastGeLFLDnGiemdiGg-p  (806)
SPINACH   nILamQgkAmTTqaARkTpFHLLVvmsdcGasfGeLFLDDGvevtmGvnR  (803)
ARABID.   eIvamQgeALTTrdaRkTpyqLLVvasrleniSGeLFLDDGenlrmGa-g  (796)

BARLEY    S---D-WSMVRFNYKIPNNKGAIKVKSEVVHNSYAQSRTLVISKVVLMGH  (816)
S.BEET    g---gkWtlVRFfsesgiN--nltisSEVVnrgYAmSqrwVmdKitilGl  (851)
SPINACH   g---k-WtfVkF--iaaeaKqtclitSdVVegefAvSqkwVIdKvtilGl  (847)
ARABID.   ggtrD-WtlVkF--rcyvtgkevvlrSEVVnpeYAekmkwelgKVtfvGf  (843)

BARLEY    RSPAAPKKLTVHVNSAEVEASSSAGTRYQNAGGLGGVAH-IGGLSLVVGE  (867)
S.BEET    krrvkiKeyIVqkdagaikvkglgrrtsshnqGgfIVsv-IedLrqlvGq  (900)
SPINACH   RkgtkingyIVrtgavtrkgdkSklkstpdrkGefiVAe-IsGLnLllGr  (896)
ARABID.   envenvKtyeVrtserlrspriSlrktvsdnddprflsvevskLSLlVCk  (893)

BARLEY    EFELKV----AMSY  (877)
S.BEET    aFkLelefegAtrv  (914)
SPINACH   EFkL-------vlh  (903)
ARABID.   kFEmrl----rlt-  (902)
```

FIG 2

MODIFIED BARLEY α-GLUCOSIDASE

CROSS-REFERENCE TO RELATED APPLICATIONS

This application claims the benefit of U.S. provisional application No. 60/260,787 filed Jan. 10, 2001.

STATEMENT REGARDING FEDERALLY SPONSORED RESEARCH OR DEVELOPMENT

To be determined.

BACKGROUND OF THE INVENTION

In the germination of seeds of cereal plants, starch degradation is an important metabolic process. Starch is the primary source of carbon and energy for cereal seedlings until they become autotrophic. Degradation of cereal starches in cereal seedlings is a result of the concerted action of several enzymes including α-amylase, β-amylase, debranching enzyme and α-glucosidase. It has been observed that during the early stages of starch hydrolysis in germinating cereal seeds, α-amylase is the most important enzyme and α-glucosidase is the second most important enzyme to the seedlings starch degradation processes.

Starch degradation processes are important for other reasons besides the viability and vigor of cereal seedlings. Many food processes involve the conversion of starch from cereal plants for food or other uses. It is known that α-glucosidase accelerates the initial hydrolysis of starch granules in the presence of α-amylase. In vitro, barley α-glucosidase can hydrolyze native starch granules at a rate comparable to α-amylase. In addition, the two enzymes act synergistically in the starch degradation process.

For food production applications, and in other industrial processes to produce or process starches from cereals, thermal stability of enzymes becomes an important criteria. For example, the thermal stability of α-glucosidase is important because the conversion of barley starch to fermentable sugars during the industrial production of ethanol, as in brewing or in fuel ethanol production, typically takes place at temperatures of 65 to 73° C. The thermal lability of many native barley α-glucosidase enzymes results in either reduced efficiency of starch break down at the higher temperatures used for starch gelatinization, or requires that the starch be cooled to a more favorable temperature for enzymatic hydrolysis after the starch is gelatinized.

Significant research has occurred on barley α-glucosidase in the last few years. In fact, the native barley gene for α-glucosidase has been sequenced, cloned, and the amino acid sequence of the resulting expressed enzyme has been determined. The DNA sequence of the native cDNA and the amino acid sequence of the protein are fully described in U.S. Pat. No. 5,763,252, the disclosure of which is incorporated herein by reference.

While the full sequence of barley α-glucosidase is known, many critical details about the structure and function of the enzyme are still uncharacterized. No crystal structure has been determined for any α-glucosidase of the glucosyl hydrolase family, making it much more difficult to intelligently select targets for mutagenesis. It is known that the α-glucosidase genes from various plants do have variations in their thermostability, but the rationales and reasons behind those differences are obscure. The lack of thermostable α-glucosidases has been a limitation in the industrial use of α-glucosidase enzymes to replace or supplement α-amylases in industrial hydrolysis systems. Thus the need exists for more thermostable α-glucosidases which can be used for a wide variety of industrial and food preparation purposes such as specifically brewing and fuel ethanol production.

BRIEF SUMMARY OF THE INVENTION

The present invention is summarized in that a barley α-glucosidase has been subjected to conservative mutation to create variants of the amino acid sequence of the native enzyme which are more thermostable and therefore more suitable for industrial purposes.

It is an object of the present invention to provide for the creation of mutant forms of barley α-glucosidase genes which encode enzymes having increased thermostability for incorporation in transgenic barley plants which are thereby more suitable for industrial utilization in processes requiring starch hydrolysis.

Other objects, advantages, and features of the present invention will become apparent from the following specification when taken in conjunction with the accompanying drawings.

BRIEF DESCRIPTION OF THE SEVERAL VIEWS OF THE DRAWINGS

FIG. 2 is a sequence alignment of the amino acid sequence of various plant α-glucosidases.

DETAILED DESCRIPTION OF THE INVENTION

Figure 1:
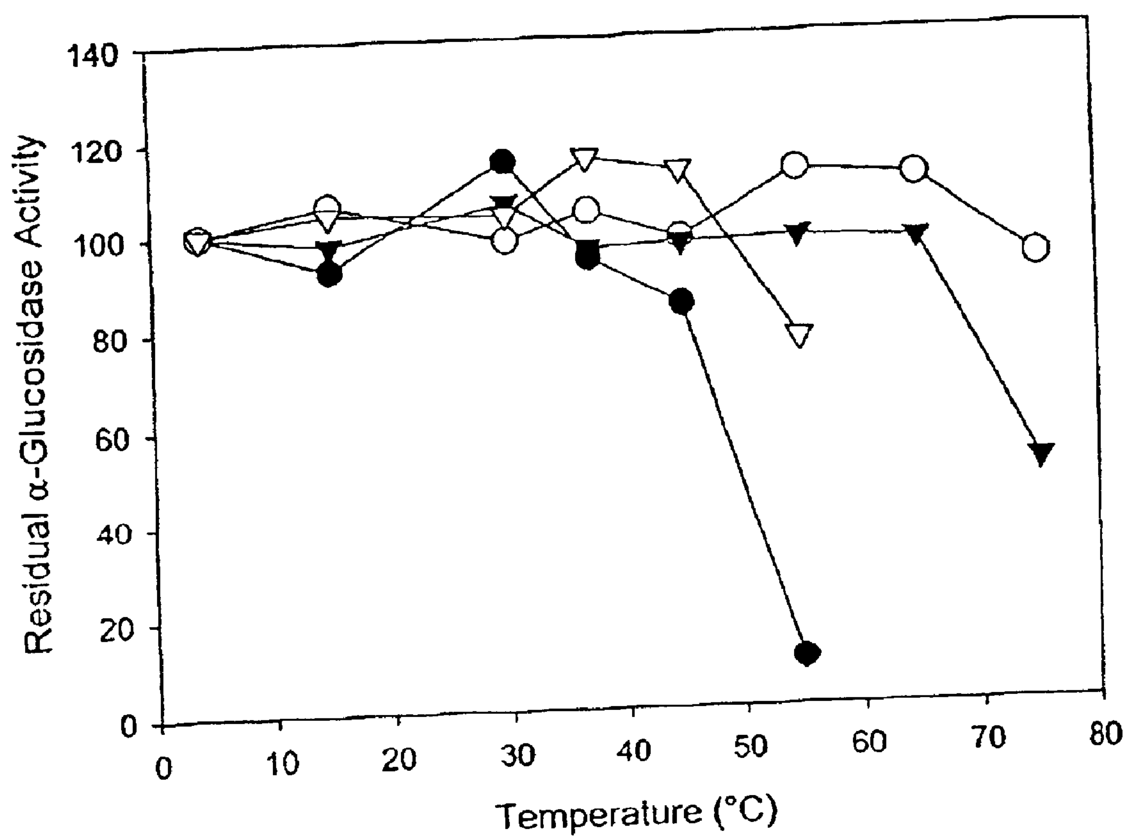
FIG. 1 is a graphical illustration of the thermostability of various plant α-glucosidase enzymes.

In order to consider directed experiments to make a barley α-glucosidase that has improved thermostability, the first problem is the lack of information. By function, the α-glucosidase enzyme is classified as a member of the glycosyl hydrolase 31 family of enzymes. Not only is there no known three-dimensional study of the structure of the α-glucosidase enzyme, there is no known crystal structure for any member of that family of enzymes. It is therefore not possible to directly study the tertiary structure of the enzyme to identify what locations might be suitable to consider for making changes to the molecule to add thermal stability. Accordingly, indirect methods were used to identify sites of directed mutagenesis where potential changes in amino acids would add to the thermal characteristics of the enzyme. To approach that question, the available information about plant α-glucosidases was examined. The literature contains the sequences of several known α-glucosidase genes from various plants. It was also known that the enzymes encoded by those genes contain significant variation in their thermostability. FIG. 1 illustrates the variation in thermostability among several known α-glucosidase isoforms. In FIG. 1, the results obtained with the α-glucosidase from barley are indicated by the closed circles, the sugar beet enzyme results are charted by the open circles, the characteristics of the spinach enzyme are shown by the closed triangle and the thermal characteristics of the Arabidopsis enzyme are illustrated by the open triangle. Each enzyme is compared to a non-heated control sample of the same enzyme. This data suggests that the barley enzyme is one of the less thermostable of known plant α-glucosidase isoforms and that it should be possible to improve its thermal characteristics. A project thus was initiated to make directed sequence modifications to the amino acid sequence of the barley α-glucosidase enzyme, the locations of the modifications being selected based on sequence comparisons to other plant α-glucosidase genes. In essence, the idea is to test modifications to the barley gene to incorporate into the enzyme amino acid residues found in other plant α-glucosidases.

To facilitate this process an alignment study of the various known plant α-glucosidase genes was conducted. This alignment is represented in an alignment table. shown in FIG. 2. FIG. 2 shows the best-fit alignment of the amino acid sequence of the α-glucosidase genes from barley, sugar beet, spinach and Arabidopsis (provided as SEQ ID NO: 1, 2, 3 and 4, respectively), using the conventional single letter representations for the amino acids. Capital letters indicate identity to the barley sequence. This sequence comparison information can be combined with information about predicted secondary structure of the protein available from computer analysis of the sequence to begin to identify sites for mutation to create better thermostability.

The data presented above demonstrated that the differences in thermostability among the plant α-glucosidase enzymes was significant. For example, the enzyme from sugar beet still retains 60% of its maximal activity following exposure to 75° C. for 10 minutes. By contrast, the native form of barley α-glucosidase retains only 10% of its maximal activity after exposure to 55° C. for 10 minutes. The spinach and Arabidopsis enzymes are between these two extremes, with the spinach enzyme being the second highest in thermostability and the Arabidopsis enzyme third. Analysis of the deduced amino acid sequences among the four enzymes showed that the barley sequence actually had a relatively high level of sequence identity with the sugar beet and spinach enzymes, 50.8% and 53.6%, respectively. Thus the differences which do exist between the barley sequence and those of sugar beet and spinach likely account for the differences in thermal behavior. So a possible approach to adding thermal stability to the barley enzyme is to make it more like the homologous enzymes from other plants. The problem then became deciding which changes to the barley sequence would have the desired effect.

One set of differences in amino acid sequence which was identified is that the sugar beet, spinach and Arabidopsis sequences had four commonly conserved proline residues not found in the barley enzyme. These residues were prolines at position 336, 340, 547 and 742 (based on the homologous position in the barley sequence). It is also known that proline residues can be important for thermostability (Suzuki, Y., Proc. Jpn. Acad. Ser. B Phys. Biol. Sci. 65: 146–148(1989)). Thus it was decided to test directed mutations of the barley sequence to add proline residues at positions 336, 340 and 742 to test this possibility. No mutation was attempted at position 547 because the secondary structure predictions made using the program Peptide Structure (Wisconsin GCG Package, Madison, Wis.) predicted that this residue is in the middle of a β-sheet. It has been reported that the addition of a proline to a β-sheet would not enhance thermostability of an enzyme (Watanabe, et al., Y. Eur. J. Biochem. 226: 2777–283 (1994)).

Based on this analysis, genes encoding mutant forms of the barley α-glucosidase enzyme were created and tested for thermostability. The native barley sequence was available, as disclosed in U.S. Pat. No. 5,763,252. Conservative changes were engineered into the native barley DNA sequence to change a single codon to code for proline in substitution for another amino acid. The genes encoding the enzymes were cloned into suitable expression vectors and expressed in yeast. The mutant enzymatic forms designated T340P (this nomenclature indicating a "T" or threonine residue at location 340 in the native sequence has been changed to a "P" or proline residue) and A742P (alanine to proline at residue 742) exhibited activity, but a similar mutation at position 336 (R336P—arginine to proline) failed to yield a protein with appropriate detectable enzymatic activity.

All three mutated enzymes were tested for thermal performance compared to the native barley enzyme. The mutant form T340P was tested first at pH 6.0. The temperature at which the wild-type enzyme showed only 50% of its activity was 48° C. By contrast the mutant enzyme isoform T340P did not show any decrease in activity until after it was heated to 50° C., and the temperature at which 50% of the activity was lost was found to be 58° C., which represents an improvement of 10° C. from the wild type. Since thermostability may be decreased in lower levels of pH, the test was repeated at a pH of 4.0, at which the temperature for a loss of 50% activity for the wild type was 36° C. and for the T340P was 43° C. A similar test at pH 6.0 was conducted with A742P, but that test did not yield an improved result for this mutant isoform at this pH.

Based on this observation, the protein sequence was studied for other possible modifications which might improve thermal stability of the wild type barley α-glucosidase. The modifications considered were those which would add prolines, remove or add glycosylation sites, or remove possible sites of deamidation or hydrolysis of peptide bonds at aspartic acid residues. Proline residues can be added because several studies show an increase in thermostability due to the addition of prolines at key sites. The mechanism of proline stabilization revolves around the presence of proline residues at the second sites of β-turns and in the first turn of α-helices (Watanabe et al., FEBS Lett. 290:221–223 (1991)). Chen et al., Protein Eng. 8:575–582 (1994) showed that the thermostability of fungal glucoamylase can be increased by decreasing the deamidation of selected asparagine-glycine sequences by substituting alanine for asparagines. Ahern and Klibinov, Science 228:1280–1284 (1985) found that the thermal inactivation of lysozyme can attributed to both the deamidation of asparagine-glycine sequences as well as the hydrolysis of aspartate-X peptide bonds. Therefore, it is envisioned that aspartic acid residues will be changed to glutamic acid residues. There is evidence that both the addition, Olsen and Thomsen, J. of General Microb. 137: 579–585 (1991), and removal, Meldgaard and Svendsen, Microbiology 140:159–1661994, of N-glycosylation has shown an increase in thermostability in various enzymes. Therefore, N-glycosylation sites will either be introduced or removed using site-directed mutagenesis.

What follows as Table 1 is a list of proposed additional mutations designed to enhance the thermostability of barley alpha-glucosidase based on the sequence alignment between the barley enzyme and the sugar beet, spinach, and Arabidopsis enzymes. These mutants will remove either deamidation sites or aspartic acids, add or remove N-glycosylation sites, or add prolines. The influence of prolines on nearby residues is so strong that the imprudent substitution of proline for another amino acid might result in the destruction of both secondary and tertiary structures, as well as the loss of protein function and stability. Therefore, prolines will only be substituted if the residue would be in the first turn of an α-helix or second site of a β-turn. Since there is no crystal structure for barley α-glucosidase the presumed presence of α-helices and β-turns is based on the secondary structure predictions using computer analysis.

TABLE 1

| | |
|---|---|
| D83E | Removing an aspartate |
| D92E | Removing an aspartate |
| G100P | Adding a proline |
| D101P | Adding a proline, Removing an aspartate |
| D105E | Removing an aspartate |
| A122P | Adding a proline |
| S184P | Adding a proline |
| N298D | Removing N-glycosylation site |
| R336P | Adding a proline |
| D369E | Removing an aspartate |
| D372N | Adding N-glycosylation site, removing an aspartate |
| N391D | Removing N-glycosylation site |
| N394P | Adding a proline |
| D403P | Adding a proline, removing an aspartate |
| D463S | Adding N-glycosylation site |
| D508E | Removing an aspartate |
| N568A | Removing a deamidation site |
| D694N | Adding N-glycosylation site, removing an aspartate |
| A713P | Adding a proline |
| A742P | Adding a proline |
| D764E | Removing an aspartate |

Since the above modifications to the native barley α-glucosidase enzyme are made without support from the analysis of the tertiary structure of the protein, some of these changes might result in decrease or absence of enzymatic activity or a change in thermal characteristics in an unwanted direction. Accordingly, each of these proposed alterations should be separately tested, as described below with the T340P mutant form. However, the data presented here demonstrates that this strategy can be successfully implemented. Since the method for selecting sites for directed mutagenesis are presented here, and since a method for testing the thermal stability is also described, it is now possible for those of skill in the field to test the mutations proposed above to determine empirically which ones add to the thermostability of the enzyme.

Techniques for site directed mutagenesis of DNA modifications are well known to those of skill in the art. In short, segments of constructed DNA of specific sequence can be substituted for segments of DNA from the native coding sequence to produce any sequence desired. It has also become common in the field to take mutant forms of coding sequences encoding proteins and clone those sequences into widely available expression vectors to express the coding sequences in a host, which can be heterologous to the native gene or not. Since protein production mechanisms are generally conserved within eukaryotic organisms, such a mutant protein can be most conveniently produced for testing its properties in whatever convenient eukaryotic expression system is available, including both host based systems, such as yeast, as well as systems based on cell-free gene expression.

It is also understood that because of the degeneracy of the genetic code, many different DNA sequences can encode the same protein. Hence, many changes to DNA sequences are possible without changing the protein produced from expression of a coding sequence. Also, it is possible to make modest conservative changes to the amino acid sequence of a protein without changing its functionality or characteristics in any significant manner. Such minor changes are within the scope of the invention claimed here. This document also contains DNA and/or protein sequences. While these sequences are believed correct, given the limits of present technology, it is possible that there might be one or more small errors, whether by insertion, substitution or deletion. However, since the sequences are certainly almost completely correct, those of skill in the art know how to work around and correct minor sequence errors of this type.

EXAMPLES

Chemicals and reagents. Chemicals were purchased from Sigma (St. Louis, Mo.) unless otherwise stated.

Plant sources. Seeds of a sugar beet breeding line (ACS9400461) were kindly provided by Professor I. Goldman (University of Wisconsin). Arabidopsis (v. Columbia) seedlings were grown under a 10 hour photoperiod at a temperature of 25° C. for 3 weeks before harvesting. Spinach seeds (cv. Bloomsdale Longstanding, Northrup King) were purchased locally. Barley seeds (cv. Morex) were imbibed, germinated and kilned as described by Henson and Stone, J. Chromatog. 469:361–367 (1989).

Isolation of crude extracts from plants. Crude extracts from malted barley, seeds of sugar beet and spinach, and leaves from Arabidopsis were isolated using published protocols (Im and Henson, Carbohydr. Res. 277:145–159 (1995); Chiba et al., Agric. Biol. Chem. 42: 241–245 (1978); Sugimoto et al., L. Biosci. Biotech. Biochem. 59: 673–677 (1995); Monroe et al., Plant Physiol. 119: 385–397 (1999)). The extracts were dialyzed (16 hours, 4° C.) against 50 mM sodium-succinate, pH 4.5.

Enzyme assay. α-Glucosidase activities were measured by the release of glucose from maltose. Unless otherwise stated, the enzyme was incubated for 1 hour at 30° C. with 25 mM maltose in 50 mM sodium-succinate (pH 4.5) during which time substrate hydrolysis rates were linear. The glucose released was quantified by determining the reduction of NAD by the coupled reactions of hexokinase and glucose-6-dehydrogenase (Im and Henson, Carbohydr. Res. 277:145–159 (1995)).

Thermostability testing of plant extracts. Enzyme extracts were incubated for 10 minutes at temperatures ranging from 5 to 75° C. The residual rate of maltose hydrolysis was assayed for 1 hour at 30° C.

Alignment of α-glucosidase sequences from four plant species. Alignment of the published α-glucosidase amino acid sequences from barley (Genbank accession number U22450), spinach (D86624), sugarbeet (D89615), and Arabidopsis (AF014806) was done using the program Align Plus-Version 2.0 (Scientific and Educational Software). The results of the alignment are shown on FIG. 2.

Mutagenesis. Mutagenesis was done using the Muta-Gene kit (BIO-RAD). Barley α-glucosidase cDNA was subcloned into the EcoRI site of the phagemid pTZ18U (BIO-RAD, Hercules, Calif.). *E. coli* strain CJ236 (Kunkel et al., 1987) was used to generate dU-substituted DNA and single stranded DNA was isolated using the helper phage M13K07 (BIO-RAD). For the mutant R336P. the oligonucleotide CGGTGAAGTTGACAGGATCCAAGGTGAAG (SEQ ID NO:5) (5', reverse complement) was used to replace the codon for arginine (CGT) with a codon for proline (CCT) and to remove a Tth 111I site. For the mutant T340P, the oligonucleotide GAGCTCGGCGGCGGGGAAGTUACACGGTC (SEQ ID NO:6) was used to replace the codon for threonine (ACC) with a codon for proline (CCC) and to remove a Tth111I site. For the mutant A742P, the oligonucleotide CCAGGAGGTGGAACGGGGTCCGGCGC (SEQ ID NO: 7) was used to replace the codon for alanine (GCG) with a codon for proline (CCG) and to remove a RsrII site.

Sequencing. The mutated cDNA was sequenced using the Sanger method with an automatic sequencer by the Interdisciplinary Center for Biotechnology Research, University of Florida, Gainesville, Fla.

Expression. The mutated cDNA was subcloned into the EcoRI sites of the *Pichia pastoris* vector pPIC9K (Invitrogen) and transformed into *P. pastoris* GS 115 using the *Pichia* EasyComp kit (Invitrogen). Ten histidine autotrophs (His+) were induced with methanol following the instructions in the *Pichia* Expression Kit (Invitrogen). *Pichia* colonies that secreted measurable α-glucosidase activity were used for thermostability studies.

Thermostability testing of wild-type and mutated α-glucosidase. Enzyme extracts from non-mutated, recombinant α-glucosidase (rAGL), T340P and A742P were incubated for 10 minutes at temperatures ranging from 0 to 60° C. at a pH of either 6.0 or 4.0. The residual rate of maltose hydrolysis was assayed for 18 hours at 30° C. at pH 4.5.

Figure 3:
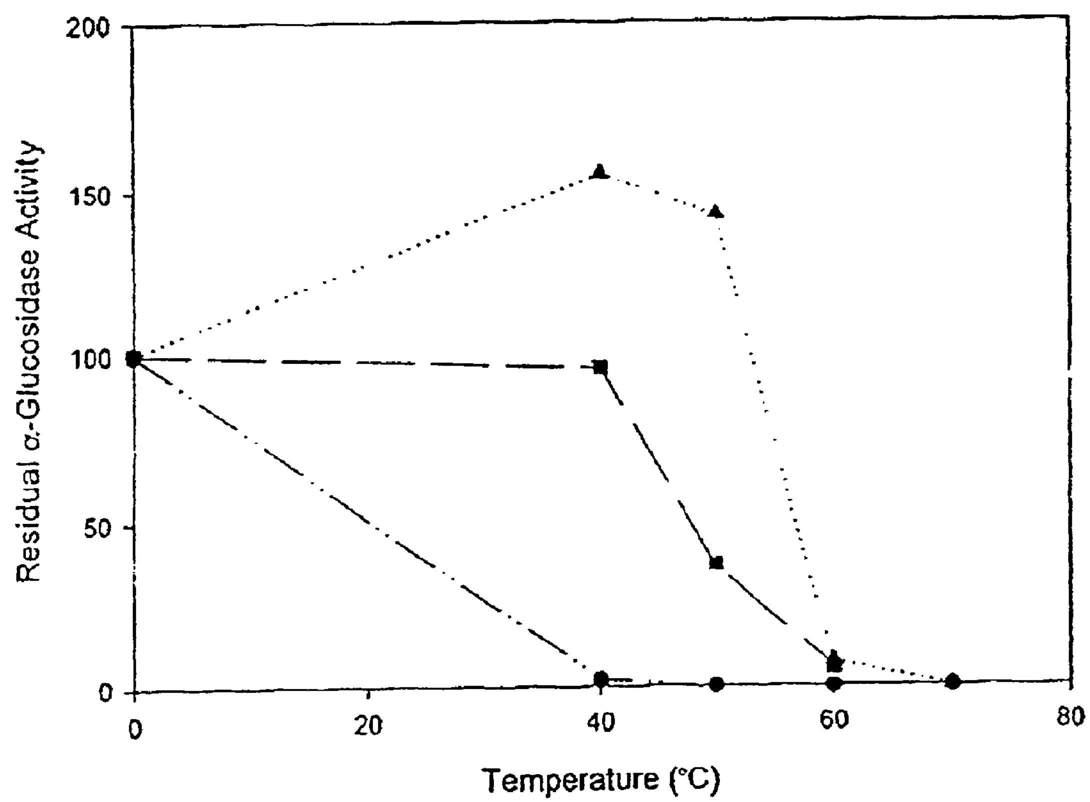
FIGS. 3, 4 and 5 are graphical illustration of some of the experimental results from the results of the examples below.
Figure 4:
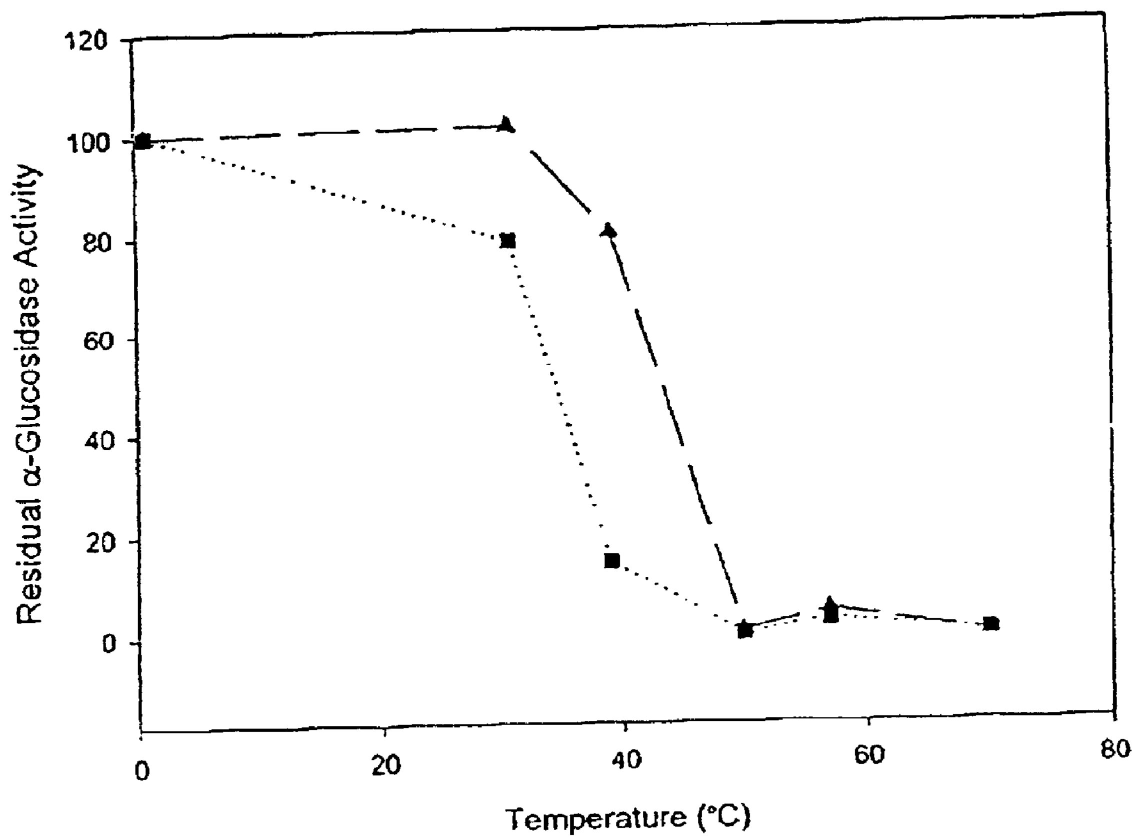
Figure 5:
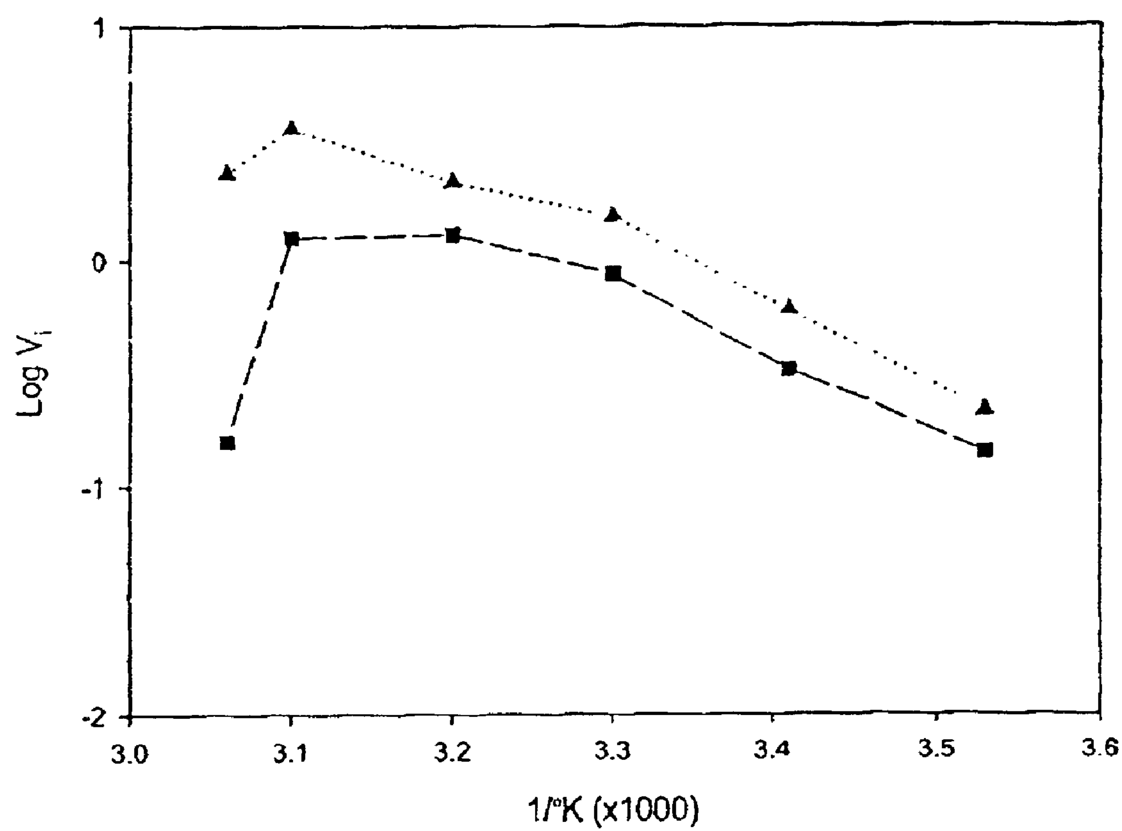

Results. FIG. 3 illustrates the improved thermostability of the T340P mutant form of the enzyme as compared to wild type barley α-glucosidase. In FIG. 3, the thermostability of the native barley α-glucosidase (squares) is compared that of the T340P enzyme (triangles) at a temperature range of up to 60° C. at a pH of 6.0. Activity is compared to the same enzyme extract unheated. FIG. 4 shows a similar test at a pH of 4.0, again with the native form indicated by squares and the T340P indicated by triangles. FIG. 5 shows an Arrhenius plot of the native and the T340P. Enzyme extracts of recombinantly produced wild-type and the T340P were incubated at temperatures from 0 to 55° C., and assayed at the same temperatures at pH of 4.5. The results are plotted as log $V_i$ vs. $10^{-3}$/T(° C.).

Mashing. The effect of the thermostable modified barley α-glucosidase was then tested in mashing. Mashing is the process whereby a nutrient solution capable of supporting fermentation by brewer's yeast is made from malted barley. The sugars that yeast ferment are glucose, maltose and maltriose. Mashing was conducted in the presence of non-modified recombinant barley α-glucosidase (designated rAGLwt, control) and in the presence of the modified T340P barley α-glucosidase. The amount of glucose produced by the mashes containing the T340P enzyme was found to be 29% greater than that produced in the control mashes. Similarly, there was 25% more maltose and 26% more maltriose in the mashes containing T340P than in mashes containing the rAGLwt. In addition, the real degree of fermentation values (RDF), calculated on a per unit α-glucosidase added to the mash, were higher in the mashes with added T340P. The mashes containing the T340P also had higher concentrations of maltotetraose, maltopentaose, maltohexaose, and maltoheptaose, but the differences may not have been statistically significant. The new results of the mashing processes demonstrated that the modified barley α-glucosidase increases the amount of fermentable sugars in real world processes, and thus provides new options for brewers to obtain desirable carbohydrate profiles in brewed products.

Transgenic plants. The gene encoding T340P can also be expressed in transgenic plants. Plant gene expression cassettes are widely available based on strong constitutive promoters, and condition and tissue specific promoters are now becoming available. The coding sequence for the T340P enzyme can be placed into such an expression cassette and transformed into barley, which is susceptible to particle mediated plant transformation techniques. Since the improvement in thermal stability in the T340P enzyme is due to the sequence modification, the enzyme expressed in transgenic barley will have the same thermal processing characteristics as the enzyme produced in the yeast described above.

Other modifications. The modified barley α-glucosidase isoforms N298D, N391D and D694N have also been constructed. The mutants N298D and N391D have been expressed in yeast and tested for thermal stability. The N298D enzyme shows increased thermostability as compared to the wild type. This demonstrates that other modifications to increase thermal stability identified in Table 1 will also be effective.

We claim:

1. A modified α-glucosidase enzyme, the modified form differing from the wild-type barley α-glucosidase by proline being substituted for the threonine residue found in the wild-type protein in the amino acid sequence Val-Asn-Phe-Thr, which are amino acids 337 through 340 of SEQ ID NO:1, the threonine located at residue 340 in SEQ ID NO:1, the modified enzyme retaining activity at a higher temperature than the wild-type enzyme.

2. A modified α-glucosidase enzyme, the modified enzyme differing from the wild-type barley α-glucosidase by an amino acid modification which confers thermal stability on the modified enzyme so that the modified enzyme retains enzymatic activity at a higher temperature than the wild-type enzyme, the modification being selected from the group consisting of adding a proline and deleting an aspartate at residue 101, deleting an aspartate at residue 105, deleting an aspartate at residue 369, adding N-glycosylation site and deleting an aspartate at residue 372, adding N-glycosylation site to residue 463, deleting an aspartate at residue 508, and adding N-glycosylation site and deleting an aspartate at residue 694, the residues referring to SEQ ID NO:1, and the residue positions determined by best-fit alignment of amino acid sequences to SEQ ID NO:1.

* * * * *

```
                          SEQUENCE LISTING

<160> NUMBER OF SEQ ID NOS: 7

<210> SEQ ID NO 1
<211> LENGTH: 877
<212> TYPE: PRT
<213> ORGANISM: Barley

<400> SEQUENCE: 1

Met Ala Thr Val Gly Val Leu Leu Leu Cys Leu Cys Leu Cys Leu Phe
  1               5                  10                  15

Ala Pro Arg Leu Cys Ser Ser Lys Glu Glu Gly Pro Leu Ala Ala Arg
             20                  25                  30

Thr Val Leu Ala Val Ala Val Thr Met Glu Gly Ala Leu Arg Ala Glu
         35                  40                  45

Ala Ala Thr Gly Gly Arg Ser Ser Thr Gly Asp Val Gln Arg Leu Ala
     50                  55                  60

Val Tyr Ala Ser Leu Glu Thr Asp Ser Arg Leu Arg Val Arg Ile Thr
 65                  70                  75                  80

Asp Ala Asp His Pro Arg Trp Glu Val Pro Gln Asp Ile Ile Pro Arg
                 85                  90                  95

Pro Ala Pro Gly Asp Val Leu His Asp Ala Pro Pro Ala Ser Ser Ala
            100                 105                 110
```

-continued

```
Pro Leu Gln Gly Arg Val Leu Ser Pro Ala Gly Ser Asp Leu Val Leu
        115                 120                 125

Thr Val His Ala Ser Pro Phe Arg Phe Thr Val Ser Arg Arg Ser Thr
    130                 135                 140

Gly Asp Thr Leu Phe Asp Thr Ala Pro Gly Leu Val Phe Arg Asp Lys
145                 150                 155                 160

Tyr Leu Glu Val Thr Ser Ala Leu Pro Ala Gly Arg Ala Ser Leu Tyr
                165                 170                 175

Gly Leu Gly Glu His Thr Lys Ser Ser Phe Arg Leu Arg His Asn Asp
            180                 185                 190

Ser Phe Thr Leu Trp Asn Ala Asp Ile Gly Ala Ser Tyr Val Asp Val
        195                 200                 205

Asn Leu Tyr Gly Ser His Pro Phe Tyr Met Asp Val Arg Ala Pro Gly
    210                 215                 220

Thr Ala His Gly Val Leu Leu Leu Ser Ser Asn Gly Met Asp Val Leu
225                 230                 235                 240

Tyr Gly Gly Ser Tyr Val Thr Tyr Lys Val Ile Gly Gly Val Leu Asp
                245                 250                 255

Phe Tyr Phe Phe Ala Gly Pro Asn Pro Leu Ala Val Val Asp Gln Tyr
            260                 265                 270

Thr Gln Leu Ile Ala Arg Pro Ala Pro Met Pro Tyr Trp Ser Phe Gly
        275                 280                 285

Phe His Gln Cys Arg Tyr Gly Tyr Leu Asn Val Ser Asp Leu Glu Arg
    290                 295                 300

Val Val Ala Arg Tyr Ala Lys Ala Arg Ile Pro Leu Glu Val Met Trp
305                 310                 315                 320

Thr Asp Ile Asp Tyr Met Asp Gly Phe Lys Asp Phe Thr Leu Asp Arg
                325                 330                 335

Val Asn Phe Thr Ala Ala Glu Leu Arg Pro Phe Val Asp Arg Leu His
            340                 345                 350

Arg Asn Ala Gln Lys Tyr Val Leu Ile Leu Asp Pro Gly Ile Arg Val
        355                 360                 365

Asp Pro Ile Asp Ala Thr Tyr Gly Thr Phe Val Arg Gly Met Gln Gln
    370                 375                 380

Asp Ile Phe Leu Lys Arg Asn Gly Thr Asn Phe Val Gly Asn Val Trp
385                 390                 395                 400

Pro Gly Asp Val Tyr Phe Pro Asp Phe Met His Pro Ala Ala Ala Glu
                405                 410                 415

Phe Trp Ala Arg Glu Ile Ser Leu Phe Arg Arg Thr Ile Pro Val Asp
            420                 425                 430

Gly Leu Trp Ile Asp Met Asn Glu Ile Ser Asn Phe Tyr Asn Pro Glu
        435                 440                 445

Pro Met Asn Ala Leu Asp Asp Pro Pro Tyr Arg Ile Asn Asn Asp Gly
    450                 455                 460

Thr Gly Arg Pro Ile Asn Asn Lys Thr Val Arg Pro Leu Ala Val His
465                 470                 475                 480

Tyr Gly Gly Val Thr Glu Tyr Glu Glu His Asn Leu Phe Gly Leu Leu
                485                 490                 495

Glu Ala Arg Ala Thr Gly Arg Gly Val Leu Arg Asp Thr Gly Arg Arg
            500                 505                 510

Pro Phe Val Leu Ser Arg Ser Thr Phe Val Gly Ser Gly Arg Tyr Thr
        515                 520                 525
```

-continued

```
Ala Tyr Trp Thr Gly Asp Asn Ala Ala Thr Trp Gly Asp Leu Arg Tyr
    530                 535                 540

Ser Ile Asn Thr Met Leu Ser Phe Gly Leu Phe Gly Met Pro Met Ile
545                 550                 555                 560

Gly Ala Asp Ile Cys Gly Phe Asn Gly Asn Thr Thr Glu Glu Leu Cys
                565                 570                 575

Gly Arg Trp Ile Gln Leu Gly Ala Phe Tyr Pro Phe Ser Arg Asp His
            580                 585                 590

Ser Ala Ile Phe Thr Val Arg Arg Glu Leu Tyr Leu Trp Pro Ser Val
        595                 600                 605

Ala Ala Ser Gly Arg Lys Ala Leu Gly Leu Arg Tyr Gln Leu Leu Pro
    610                 615                 620

Tyr Phe Tyr Thr Leu Met Tyr Glu Ala His Met Thr Gly Ala Pro Ile
625                 630                 635                 640

Ala Arg Pro Leu Phe Phe Ser Tyr Pro His Asp Val Ala Thr Tyr Gly
                645                 650                 655

Val Asp Arg Gln Phe Leu Leu Gly Arg Gly Val Leu Val Ser Pro Val
            660                 665                 670

Leu Glu Pro Gly Pro Thr Thr Val Asp Ala Tyr Phe Pro Ala Gly Arg
        675                 680                 685

Trp Tyr Arg Leu Tyr Asp Tyr Ser Leu Ala Val Ala Thr Arg Thr Gly
    690                 695                 700

Lys His Val Arg Leu Pro Ala Pro Ala Asp Thr Val Asn Val His Leu
705                 710                 715                 720

Thr Gly Gly Thr Ile Leu Pro Leu Gln Gln Ser Ala Leu Thr Thr Ser
                725                 730                 735

Arg Ala Arg Arg Thr Ala Phe His Leu Leu Val Ala Leu Ala Glu Asp
            740                 745                 750

Gly Thr Ala Ser Gly Tyr Leu Phe Leu Asp Asp Gly Asp Ser Pro Glu
        755                 760                 765

Tyr Gly Arg Arg Ser Asp Trp Ser Met Val Arg Phe Asn Tyr Lys Ile
    770                 775                 780

Pro Asn Asn Lys Gly Ala Ile Lys Val Lys Ser Glu Val Val His Asn
785                 790                 795                 800

Ser Tyr Ala Gln Ser Arg Thr Leu Val Ile Ser Lys Val Val Leu Met
                805                 810                 815

Gly His Arg Ser Pro Ala Ala Pro Lys Lys Leu Thr Val His Val Asn
            820                 825                 830

Ser Ala Glu Val Glu Ala Ser Ser Ser Ala Gly Thr Arg Tyr Gln Asn
        835                 840                 845

Ala Gly Gly Leu Gly Gly Val Ala His Ile Gly Gly Leu Ser Leu Val
    850                 855                 860

Val Gly Glu Glu Phe Glu Leu Lys Val Ala Met Ser Tyr
865                 870                 875


<210> SEQ ID NO 2
<211> LENGTH: 914
<212> TYPE: PRT
<213> ORGANISM: Sugar beet

<400> SEQUENCE: 2

Met Glu Arg Ser Lys Leu Pro Arg Tyr Ile Cys Pro Thr Leu Ala Val
  1               5                  10                  15

Val Leu Pro Leu Val Leu Cys Met Val Val Glu Gly Ala Thr Thr Ser
             20                  25                  30
```

-continued

```
Lys Asn Asp Asn Gln Gly Glu Ala Ile Gly Tyr Gly Tyr Gln Val Lys
         35                  40                  45

Asn Ala Lys Val Asp Asn Ser Thr Gly Lys Ser Leu Thr Ala Leu Leu
     50                  55                  60

Gln Leu Ile Arg Asn Ser Pro Val Tyr Gly Pro Asp Ile His Phe Leu
 65                  70                  75                  80

Ser Phe Thr Ala Ser Phe Glu Glu Asp Asp Thr Leu Arg Ile Arg Phe
                 85                  90                  95

Thr Asp Ala Asn Asn Arg Arg Trp Glu Ile Pro Asn Glu Val Leu Pro
            100                 105                 110

Arg Pro Pro Pro Pro Pro Ser Pro Pro Pro Leu Ser Ser Leu Gln His
        115                 120                 125

Leu Pro Lys Pro Ile Pro Gln Asn Gln Pro Thr Thr Thr Val Leu Ser
    130                 135                 140

His Pro His Ser Asp Leu Ala Phe Thr Leu Phe His Thr Thr Pro Phe
145                 150                 155                 160

Gly Phe Thr Ile Tyr Arg Lys Ser Thr His Asp Val Leu Phe Asp Ala
                165                 170                 175

Thr Pro Ile Pro Ser Asn Pro Thr Thr Phe Leu Ile Tyr Lys Asp Gln
            180                 185                 190

Tyr Leu Gln Leu Ser Ser Ser Leu Pro Ala Gln Gln Ala His Leu Tyr
        195                 200                 205

Gly Leu Gly Glu His Thr Lys Pro Thr Phe Gln Leu Ala His Asn Gln
    210                 215                 220

Ile Leu Thr Leu Trp Asn Ala Asp Ile Ala Ser Phe Asn Arg Asp Leu
225                 230                 235                 240

Asn Leu Tyr Gly Ser His Pro Phe Tyr Met Asp Val Arg Ser Ser Pro
                245                 250                 255

Met Val Gly Ser Thr His Gly Val Phe Leu Leu Asn Ser Asn Gly Met
            260                 265                 270

Asp Val Glu Tyr Thr Gly Asp Arg Ile Thr Tyr Lys Val Ile Gly Gly
        275                 280                 285

Ile Ile Asp Leu Tyr Ile Phe Ala Gly Arg Thr Pro Glu Met Val Leu
    290                 295                 300

Asp Gln Tyr Thr Lys Leu Ile Gly Arg Pro Ala Pro Met Pro Tyr Trp
305                 310                 315                 320

Ala Phe Gly Phe His Gln Cys Arg Trp Gly Tyr Arg Asp Val Asn Glu
                325                 330                 335

Ile Glu Thr Val Val Asp Lys Tyr Ala Glu Ala Arg Ile Pro Leu Glu
            340                 345                 350

Val Met Trp Thr Asp Ile Asp Tyr Met Asp Ala Phe Lys Asp Phe Thr
        355                 360                 365

Leu Asp Pro Val His Phe Pro Leu Asp Lys Met Gln Gln Phe Val Thr
    370                 375                 380

Lys Leu His Arg Asn Gly Gln Arg Tyr Val Pro Ile Leu Asp Pro Gly
385                 390                 395                 400

Ile Asn Thr Asn Lys Ser Tyr Gly Thr Phe Ile Arg Gly Met Gln Ser
                405                 410                 415

Asn Val Phe Ile Lys Arg Asn Gly Asn Pro Tyr Leu Gly Ser Val Trp
            420                 425                 430

Pro Gly Pro Val Tyr Tyr Pro Asp Phe Leu Asp Pro Ala Ala Arg Ser
        435                 440                 445
```

-continued

```
Phe Trp Val Asp Glu Ile Lys Arg Phe Arg Asp Ile Leu Pro Ile Asp
    450                 455                 460

Gly Ile Trp Ile Asp Met Asn Glu Ala Ser Asn Phe Ile Thr Ser Ala
465                 470                 475                 480

Pro Thr Pro Gly Ser Thr Leu Asp Asn Pro Pro Tyr Lys Ile Asn Asn
                485                 490                 495

Ser Gly Gly Arg Val Pro Ile Asn Ser Lys Thr Ile Pro Ala Thr Ala
            500                 505                 510

Met His Tyr Gly Asn Val Thr Glu Tyr Asn Ala His Asn Leu Tyr Gly
        515                 520                 525

Phe Leu Glu Ser Gln Ala Thr Arg Glu Ala Leu Val Arg Pro Ala Thr
    530                 535                 540

Arg Gly Pro Phe Leu Leu Ser Arg Ser Thr Phe Ala Gly Ser Gly Lys
545                 550                 555                 560

Tyr Thr Ala His Trp Thr Gly Asp Asn Ala Ala Arg Trp Asp Asp Leu
                565                 570                 575

Gln Tyr Ser Ile Pro Thr Met Leu Asn Phe Gly Leu Phe Gly Met Pro
            580                 585                 590

Met Ile Gly Ala Asp Ile Cys Gly Phe Ala Glu Ser Thr Thr Glu Glu
        595                 600                 605

Leu Cys Cys Arg Trp Ile Gln Leu Gly Ala Phe Tyr Pro Phe Ser Arg
    610                 615                 620

Asp His Ser Ala Arg Asp Thr Thr His Gln Glu Leu Tyr Leu Trp Glu
625                 630                 635                 640

Ser Val Ala Ala Ser Ala Arg Thr Val Leu Gly Leu Arg Tyr Glu Leu
                645                 650                 655

Leu Pro Tyr Tyr Tyr Thr Leu Met Tyr Asp Ala Asn Leu Arg Gly Ser
            660                 665                 670

Pro Ile Ala Arg Pro Leu Ser Phe Thr Phe Pro Asp Asp Val Ala Thr
        675                 680                 685

Tyr Gly Ile Ser Ser Gln Phe Leu Ile Gly Arg Gly Ile Met Val Ser
    690                 695                 700

Pro Val Leu Gln Pro Gly Ser Ser Ile Val Asn Ala Tyr Ser Pro Arg
705                 710                 715                 720

Gly Asn Trp Val Ser Leu Ser Asn Tyr Thr Ser Ser Val Ser Val Ser
                725                 730                 735

Ala Gly Thr Tyr Val Ser Leu Ser Ala Pro Pro Asp His Ile Asn Val
            740                 745                 750

His Ile His Glu Gly Asn Ile Val Ala Met Gln Gly Glu Ala Met Thr
        755                 760                 765

Thr Gln Ala Ala Arg Ser Thr Pro Phe His Leu Leu Val Val Met Ser
    770                 775                 780

Asp His Val Ala Ser Thr Gly Glu Leu Phe Leu Asp Asn Gly Ile Glu
785                 790                 795                 800

Met Asp Ile Gly Gly Pro Gly Gly Lys Trp Thr Leu Val Arg Phe Phe
                805                 810                 815

Ala Glu Ser Gly Ile Asn Asn Leu Thr Ile Ser Ser Glu Val Val Asn
            820                 825                 830

Arg Gly Tyr Ala Met Ser Gln Arg Trp Val Met Asp Lys Ile Thr Ile
        835                 840                 845

Leu Gly Leu Lys Arg Arg Val Lys Ile Lys Glu Tyr Thr Val Gln Lys
    850                 855                 860

Asp Ala Gly Ala Ile Lys Val Lys Gly Leu Gly Arg Arg Thr Ser Ser
```

-continued

```
865                 870                 875                 880

His Asn Gln Gly Gly Phe Phe Val Ser Val Ile Ser Asp Leu Arg Gln
                885                 890                 895

Leu Val Gly Gln Ala Phe Lys Leu Glu Leu Glu Phe Glu Gly Ala Thr
            900                 905                 910

Arg Val


<210> SEQ ID NO 3
<211> LENGTH: 903
<212> TYPE: PRT
<213> ORGANISM: Spinach

<400> SEQUENCE: 3

Met Lys Lys Lys Ile Pro Ser Leu Ala Leu Gly Ile Leu Leu Val Phe
  1               5                  10                  15

Leu Leu Gln Tyr Leu Val Ala Gly Ile Ser Thr Ser Glu Asn Asp Pro
            20                  25                  30

Glu Gly Val Ile Gly Tyr Gly Tyr Lys Val Lys Ser Val Lys Val Asp
        35                  40                  45

Ser Gly Thr Arg Arg Ser Leu Thr Ala Leu Pro Gln Leu Val Lys Asn
     50                  55                  60

Ser Ser Val Tyr Gly Pro Asp Ile Gln Leu Leu Ser Ile Thr Ala Ser
 65                  70                  75                  80

Leu Glu Ser Asn Asp Arg Leu Arg Val Arg Ile Thr Asp Ala Lys His
                 85                  90                  95

Arg Arg Trp Glu Ile Pro Asp Asn Ile Leu His Arg His Gln Pro Pro
            100                 105                 110

Pro Pro Pro Pro His Ser Leu Ser Ser Leu Tyr Arg Thr Leu Leu Ser
        115                 120                 125

Ser Pro Thr Thr Asn Arg Arg Lys Ile Leu Leu Ser His Pro Asn Ser
    130                 135                 140

Asp Leu Thr Phe Ser Leu Ile Asn Thr Thr Pro Phe Gly Phe Thr Ile
145                 150                 155                 160

Ser Arg Lys Ser Thr His Asp Val Leu Phe Asp Ala Thr Pro Asp Pro
                165                 170                 175

Thr Asn Pro Asn Thr Phe Leu Ile Phe Ile Asp Gln Tyr Leu His Leu
            180                 185                 190

Thr Ser Ser Leu Pro Gly Thr Arg Ala His Ile Tyr Gly Leu Gly Glu
        195                 200                 205

His Ser Lys Pro Thr Phe Gln Leu Ala His Asn Gln Thr Leu Thr Met
    210                 215                 220

Arg Ala Ala Asp Ile Pro Ser Ser Asn Pro Asp Val Asn Leu Tyr Gly
225                 230                 235                 240

Ser His Pro Phe Tyr Met Asp Val Arg Ser Ser Pro Val Ala Gly Ser
                245                 250                 255

Thr His Gly Val Leu Leu Leu Asn Ser Asn Gly Met Asp Val Glu Tyr
            260                 265                 270

Thr Gly Asn Arg Ile Thr Tyr Lys Val Ile Gly Gly Ile Ile Asp Leu
        275                 280                 285

Tyr Phe Phe Ala Gly Pro Ser Pro Gly Gln Val Val Glu Gln Phe Thr
    290                 295                 300

Arg Val Ile Gly Arg Pro Ala Pro Met Pro Tyr Trp Ala Phe Gly Phe
305                 310                 315                 320

Gln Gln Cys Arg Tyr Gly Tyr His Asp Val Tyr Glu Leu Gln Ser Val
```

-continued

```
                325                 330                 335

Val Ala Gly Tyr Ala Lys Ala Lys Ile Pro Leu Glu Val Met Trp Thr
            340                 345                 350

Asp Ile Asp Tyr Met Asp Ala Tyr Lys Asp Phe Thr Leu Asp Pro Val
        355                 360                 365

Asn Phe Pro Leu Asp Lys Met Lys Lys Phe Val Asn Asn Leu His Lys
    370                 375                 380

Asn Gly Gln Lys Tyr Val Val Ile Leu Asp Pro Gly Ile Ser Thr Asn
385                 390                 395                 400

Lys Thr Tyr Glu Thr Tyr Ile Arg Gly Met Lys His Asp Val Phe Leu
                405                 410                 415

Lys Arg Asn Gly Lys Pro Tyr Leu Gly Ser Val Trp Pro Gly Pro Val
            420                 425                 430

Tyr Phe Pro Asp Phe Leu Lys Pro Ser Ala Leu Thr Phe Trp Thr Asp
        435                 440                 445

Glu Ile Lys Arg Phe Leu Asn Leu Leu Pro Val Asp Gly Leu Trp Ile
    450                 455                 460

Asp Met Asn Glu Ile Ser Asn Phe Ile Ser Ser Pro Pro Ile Pro Gly
465                 470                 475                 480

Ser Thr Leu Asp Asn Pro Pro Tyr Lys Ile Asn Asn Ser Gly Val Met
                485                 490                 495

Leu Pro Ile Ile Asn Lys Thr Ile Pro Pro Thr Ala Met His Tyr Gly
            500                 505                 510

Asp Ile Pro Glu Tyr Asn Val His Asn Leu Phe Gly Tyr Leu Glu Ala
        515                 520                 525

Arg Val Thr Arg Ala Ala Leu Ile Lys Leu Thr Glu Lys Arg Pro Phe
    530                 535                 540

Val Leu Ser Arg Ser Thr Phe Ser Gly Ser Gly Lys Tyr Thr Ala His
545                 550                 555                 560

Trp Thr Gly Asp Asn Ala Ala Thr Trp Asn Asp Leu Val Tyr Ser Ile
                565                 570                 575

Pro Ser Met Leu Asp Phe Gly Leu Phe Gly Ile Pro Met Val Gly Ala
            580                 585                 590

Asp Ile Cys Gly Phe Leu Gly Asn Thr Thr Glu Glu Leu Cys Arg Arg
        595                 600                 605

Trp Ile Gln Leu Gly Ala Phe Tyr Pro Phe Ser Arg Asp His Ser Ser
    610                 615                 620

Leu Gly Thr Thr Tyr Gln Glu Leu Tyr Arg Trp Glu Ser Val Ala Ala
625                 630                 635                 640

Ser Ala Arg Lys Val Leu Gly Leu Arg Tyr Thr Leu Leu Pro Tyr Phe
                645                 650                 655

Tyr Thr Leu Met Tyr Glu Ala Gln Leu Asn Gly Ile Pro Ile Ala Arg
            660                 665                 670

Pro Leu Phe Phe Ser Phe Pro Asp Asp Ile Lys Thr Tyr Gly Ile Ser
        675                 680                 685

Ser Gln Phe Leu Leu Gly Lys Gly Val Met Val Ser Pro Val Leu Lys
    690                 695                 700

Pro Gly Val Val Ser Val Thr Ala Tyr Phe Pro Arg Gly Asn Trp Phe
705                 710                 715                 720

Asp Leu Phe Asp Tyr Thr Arg Ser Val Thr Ala Ser Thr Gly Arg Tyr
                725                 730                 735

Val Thr Leu Ser Ala Pro Pro Asp His Ile Asn Val His Ile Gln Glu
            740                 745                 750
```

```
Gly Asn Ile Leu Ala Met Gln Gly Lys Ala Met Thr Thr Gln Ala Ala
        755                 760                 765

Arg Lys Thr Pro Phe His Leu Leu Val Val Met Ser Asp Cys Gly Ala
    770                 775                 780

Ser Phe Gly Glu Leu Phe Leu Asp Asp Gly Val Glu Val Thr Met Gly
785                 790                 795                 800

Val Asn Arg Gly Lys Trp Thr Phe Val Lys Phe Ile Ala Ala Ser Ala
                805                 810                 815

Lys Gln Thr Cys Ile Ile Thr Ser Asp Val Val Ser Gly Glu Phe Ala
            820                 825                 830

Val Ser Gln Lys Trp Val Ile Asp Lys Val Thr Ile Leu Gly Leu Arg
        835                 840                 845

Lys Gly Thr Lys Ile Asn Gly Tyr Thr Val Arg Thr Gly Ala Val Thr
    850                 855                 860

Arg Lys Gly Asp Lys Ser Lys Leu Lys Ser Thr Pro Asp Arg Lys Gly
865                 870                 875                 880

Glu Phe Ile Val Ala Glu Ile Ser Gly Leu Asn Leu Leu Leu Gly Arg
                885                 890                 895

Glu Phe Lys Leu Val Leu His
            900


<210> SEQ ID NO 4
<211> LENGTH: 902
<212> TYPE: PRT
<213> ORGANISM: Arabidopsis

<400> SEQUENCE: 4

Met Ser Ser Leu His Trp Phe Pro Asn Ile Phe Ile Val Val Val Val
  1               5                  10                  15

Phe Phe Ser Leu Arg Ser Ser Gln Val Val Leu Glu Glu Glu Glu Ser
            20                  25                  30

Thr Val Val Gly Tyr Gly Tyr Val Val Arg Ser Val Gly Val Asp Ser
        35                  40                  45

Asn Arg Gln Val Leu Thr Ala Lys Leu Asp Leu Ile Lys Pro Ser Ser
     50                  55                  60

Val Tyr Ala Pro Asp Ile Lys Ser Leu Asn Leu His Val Ser Leu Glu
 65                  70                  75                  80

Thr Ser Glu Arg Leu Arg Ile Arg Ile Thr Asp Ser Ser Gln Gln Arg
                85                  90                  95

Trp Glu Ile Pro Glu Thr Val Ile Pro Arg Ala Gly Asn His Ser Pro
            100                 105                 110

Arg Arg Phe Ser Thr Glu Glu Asp Gly Gly Asn Ser Pro Glu Asn Asn
        115                 120                 125

Phe Leu Ala Asp Pro Ser Ser Asp Leu Val Phe Thr Leu His Asn Thr
    130                 135                 140

Thr Pro Phe Gly Phe Ser Val Ser Arg Arg Ser Ser Gly Asp Ile Leu
145                 150                 155                 160

Phe Asp Thr Ser Pro Asp Ser Ser Asp Ser Asn Thr Tyr Phe Ile Phe
                165                 170                 175

Lys Asp Gln Phe Leu Gln Leu Ser Ser Ala Leu Pro Glu Asn Arg Ser
            180                 185                 190

Asn Leu Tyr Gly Ile Gly Glu His Thr Lys Arg Ser Phe Arg Leu Ile
        195                 200                 205

Pro Gly Glu Thr Met Thr Leu Trp Asn Ala Asp Ile Gly Ser Glu Asn
```

-continued

```
    210                 215                 220

Pro Asp Val Asn Leu Tyr Gly Ser His Pro Phe Tyr Met Asp Val Arg
225                 230                 235                 240

Gly Ser Lys Gly Asn Glu Glu Ala Gly Thr Thr His Gly Val Leu Leu
                245                 250                 255

Leu Asn Ser Asn Gly Met Asp Val Lys Tyr Glu Gly His Arg Ile Thr
            260                 265                 270

Tyr Asn Val Ile Gly Gly Val Ile Asp Leu Tyr Val Phe Ala Gly Pro
        275                 280                 285

Ser Pro Glu Met Val Met Asn Gln Tyr Thr Glu Leu Ile Gly Arg Pro
    290                 295                 300

Ala Pro Met Pro Tyr Trp Ser Phe Gly Phe His Gln Cys Arg Tyr Gly
305                 310                 315                 320

Tyr Lys Asn Val Ser Asp Leu Glu Tyr Val Val Asp Gly Tyr Ala Lys
                325                 330                 335

Ala Gly Ile Pro Leu Glu Val Met Trp Thr Asp Ile Asp Tyr Met Asp
            340                 345                 350

Gly Tyr Lys Asp Phe Thr Leu Asp Pro Val Asn Phe Pro Glu Asp Lys
        355                 360                 365

Met Gln Ser Phe Val Asp Thr Leu His Lys Asn Gly Gln Lys Tyr Val
    370                 375                 380

Leu Ile Leu Asp Pro Gly Ile Gly Val Asp Ser Ser Tyr Gly Thr Tyr
385                 390                 395                 400

Asn Arg Gly Met Glu Ala Asp Val Phe Ile Lys Arg Asn Gly Glu Pro
                405                 410                 415

Tyr Leu Gly Glu Val Trp Pro Gly Lys Val Tyr Phe Pro Asp Phe Leu
            420                 425                 430

Asn Pro Ala Ala Ala Thr Phe Trp Ser Asn Glu Ile Lys Met Phe Gln
        435                 440                 445

Glu Ile Leu Pro Leu Asp Gly Leu Trp Ile Asp Met Asn Glu Leu Ser
    450                 455                 460

Asn Phe Ile Thr Ser Pro Leu Ser Ser Gly Ser Ser Leu Asp Asp Pro
465                 470                 475                 480

Pro Tyr Lys Ile Asn Asn Ser Gly Asp Lys Arg Pro Ile Asn Asn Lys
                485                 490                 495

Thr Val Pro Ala Thr Ser Ile His Phe Gly Asn Ile Ser Glu Tyr Asp
            500                 505                 510

Ala His Asn Leu Tyr Gly Leu Leu Glu Ala Lys Ala Thr His Gln Ala
        515                 520                 525

Val Val Asp Ile Thr Gly Lys Arg Pro Phe Ile Leu Ser Arg Ser Thr
    530                 535                 540

Phe Val Ser Ser Gly Lys Tyr Thr Ala His Trp Thr Gly Asp Asn Ala
545                 550                 555                 560

Ala Lys Trp Glu Asp Leu Ala Tyr Ser Ile Pro Gly Ile Leu Asn Phe
                565                 570                 575

Gly Leu Phe Gly Ile Pro Met Val Gly Ala Asp Ile Cys Gly Phe Ser
            580                 585                 590

His Asp Thr Thr Glu Glu Leu Cys Arg Arg Trp Ile Gln Leu Gly Ala
        595                 600                 605

Phe Tyr Pro Phe Ala Arg Asp His Ser Ser Leu Gly Thr Ala Arg Gln
    610                 615                 620

Glu Leu Tyr Leu Trp Asp Ser Val Ala Ser Ser Ala Arg Lys Val Leu
625                 630                 635                 640
```

-continued

```
Gly Leu Arg Met Arg Leu Leu Pro His Leu Tyr Thr Leu Met Tyr Glu
                645                 650                 655

Ala His Val Ser Gly Asn Pro Ile Ala Arg Pro Leu Phe Phe Ser Phe
            660                 665                 670

Pro Gln Asp Thr Lys Thr Tyr Glu Ile Asp Ser Gln Phe Leu Ile Gly
        675                 680                 685

Lys Ser Ile Met Val Ser Pro Ala Leu Lys Gln Gly Ala Val Ala Val
    690                 695                 700

Asp Ala Tyr Phe Pro Ala Gly Asn Trp Phe Asp Leu Phe Asn Tyr Ser
705                 710                 715                 720

Phe Ala Val Gly Gly Asp Ser Gly Lys His Val Arg Leu Asp Thr Pro
                725                 730                 735

Ala Asp His Val Asn Val His Val Arg Glu Gly Ser Ile Val Ala Met
            740                 745                 750

Gln Gly Glu Ala Leu Thr Thr Arg Asp Ala Arg Lys Thr Pro Tyr Gln
        755                 760                 765

Leu Leu Val Val Ala Ser Arg Leu Glu Asn Ile Ser Gly Glu Leu Phe
    770                 775                 780

Leu Asp Asp Gly Glu Asn Leu Arg Met Gly Ala Gly Gly Gly Asn Arg
785                 790                 795                 800

Asp Trp Thr Leu Val Lys Phe Arg Cys Tyr Val Thr Gly Lys Ser Val
                805                 810                 815

Val Leu Arg Ser Glu Val Val Asn Pro Glu Tyr Ala Ser Lys Met Lys
            820                 825                 830

Trp Ser Ile Gly Lys Val Thr Phe Val Gly Phe Glu Asn Val Glu Asn
        835                 840                 845

Val Lys Thr Tyr Glu Val Arg Thr Ser Glu Arg Leu Arg Ser Pro Arg
    850                 855                 860

Ile Ser Leu Ile Lys Thr Val Ser Asp Asn Asp Asp Pro Arg Phe Leu
865                 870                 875                 880

Ser Val Glu Val Ser Lys Leu Ser Leu Leu Val Gly Lys Lys Phe Glu
                885                 890                 895

Met Arg Leu Arg Leu Thr
            900


<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 5

cggtgaagtt gacaggatcc aaggtgaag                                     29


<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 6

gagctcggcg gcggggaagt ttacacggtc                                    30
```

-continued

```
<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 7

ccaggaggtg gaacggggtc cggcgc                                          26
```